United States Patent
Junker et al.

Patent Number: 6,161,425
Date of Patent: Dec. 19, 2000

[54] PROCESS AND DEVICE FOR CHECKING A HOLLOW BODY SECTION

[75] Inventors: Gerd Junker, Ratingen; Gerhard Knauf, Duisburg; Ronald Claus, Welver, all of Germany

[73] Assignee: Mannesmann AG, Düsseldorf, Germany

[21] Appl. No.: 09/171,023

[22] PCT Filed: Apr. 11, 1997

[86] PCT No.: PCT/DE97/00765

§ 371 Date: Nov. 16, 1998

§ 102(e) Date: Nov. 16, 1998

[87] PCT Pub. No.: WO97/38296

PCT Pub. Date: Oct. 16, 1997

[30] Foreign Application Priority Data

Apr. 11, 1996 [DE] Germany .................... 196 16 137

[51] Int. Cl.⁷ ............... G01M 3/04; G01N 19/08
[52] U.S. Cl. .............................. 73/49.5; 73/799
[58] Field of Search ..................... 73/865.9, 744, 73/700, 45.4, 49.4, 49.5, 49.6, 49.8, 799, 807, 816

[56] References Cited

U.S. PATENT DOCUMENTS 4,154,092  5/1979  White et al. ................... 73/49.3

*Primary Examiner*—Benjamin R. Fuller
*Assistant Examiner*—Abdullahi Aw-Musse
*Attorney, Agent, or Firm*—Cohen, Pontani, Lieberman & Pavane

[57] ABSTRACT

The invention relates to a process for checking a hollow body section, wherein the section, after being filled with a fluid, is subjected to a bursting test to demonstrate its brittle fracture resistance. After the open ends of the section are closed, the required bursting pressure is applied by the dynamic movement toward each other of two elements that reach in a sealing manner through the open ends. The dynamic movement of the two elements is achieved by accelerating a weight toward one of the two elements such that the weight impacts the one of the two elements at an impact velocity, causing the dynamic movement.

7 Claims, 1 Drawing Sheet

PROCESS AND DEVICE FOR CHECKING A HOLLOW BODY SECTION

BACKGROUND OF THE INVENTION

1. Field of the Invention

The invention relates to a process for pressure checking a hollow body section.

2. Description of the Prior Art

Hollow body sections are subjected to a bursting test to check their brittle fracture resistance and/or material properties. For this purpose, the two open ends are closed by bottoms and provided with a filling-and-emptying connection. After the interior is filled with a fluid, the pressure is increased by means of a pump until bursting occurs. The circumferential strain, fracture area formation and, if required, bursting pressure are then evaluated. For the serial inspection of hollow body sections, such, for example, as airbag tubes, the process is very complex and time-consuming. Moreover, this conventional process cannot simulate a dynamic internal pressure load.

JP 58-167937 (A) in "Pat. Abstr. of Japan, Sect. P, Vol. 8 (1984) No. 1 (P-246)" discloses a process for pressure checking a hollow body section. One end of the test item stands on an abutment, while a piston of a hydraulic cylinder engages into the opposite open end. The hollow space of the test item is filled with soft rubber, and piston-like sealing rings of hard rubber are placed at the top and bottom to prevent the soft rubber from flowing off in the gap between the interior surface of the test item and the piston of the hydraulic cylinder. Pressure is applied to the piston-cylinder unit to produce an axial force on the soft rubber. This axial force creates an internal pressure in the test item, which pressure is increased until a plastic flow occurs. The material characteristic values that result are then found. Dynamic component checking is not possible with this arrangement, because the soft rubber has high compressibility and viscosity compared with a liquid. Nor can high load application speeds be produced with a hydraulic piston-cylinder unit. It is also disadvantageous that the soft rubber becomes brittle at low testing temperatures.

DE 3504685 C2 discloses a process and a device for checking the internal pressure of a tube, especially a protecting tube. The protecting tube to be checked is clamped tightly at both ends in a testing device that resembles a turning machine. A cylindrical filling piece and, at a distance therefrom, a plug are inserted into the hollow space of the protecting tube. Because the external diameter of the plug is somewhat smaller than the internal diameter of the protecting tube, a continuous annular gap is created. The plug, which extends through the left end piece, is suddenly moved in the direction of the protecting tube by a suitable hydraulic device, so that a pressure of up to 80,000 bar is built up in the liquid enclosed between the filling piece and the plug. This pressure is reduced via the annular gap along the protecting tube to the previously applied precompression of approximately 200 bar. This process allows protecting tubes to be subjected to a deliberate pressure check in keeping with their later load. It is not a bursting test to determine the toughness properties of tubular bodies. The testing device needed for this prior art pressure test is complicated and specialized for the testing of protecting tubes.

Another device for testing hollow bodies, especially weapon tubes, is disclosed in DE 2700600 A1. This device is used to determine the pressure resistance, expansion, heating and degree of erosion of the test item. No determination of toughness or testing of fracture behavior is called for. The dynamic pressurization of the tubular test item is carried out by means of propellant gas, hydropulsers or explosive charges, so that devices for these purposes are required. The end regions of the tubular test item are clamped by holders and sleeves in a force-locking and sealing manner.

DE 38 27 080 A1 discloses a process and a device for the dynamic internal pressure testing of hollow bodies, especially protecting tubes. In this process, a dynamic pressure curve relevant to the expected load is produced by means of a piston that closes an opening of the hollow body, and the stresses that occur, particularly the strains, are measured. The hollow body that closable with the piston, together with an elastic intermediate member that interacts with the hollow body in the impact direction, is loaded by means of two colliding masses. Neither this known process nor the disclosed device is suitable for a bursting test. Moreover, the test setup involves expensive apparatus and cannot be set up everywhere.

SUMMARY OF THE INVENTION

The object of the present invention is to provide a process for checking a hollow body section that can be implemented with a simple device economically and quickly, particularly for serial parts, and that supplies highly realistic results in simulating dynamic internal pressure loading.

This object is attained by a process for pressure checking a hollow body section having a first open end and a second open end including sealingly closing the first open end by movably inserting a first element in the first open end, filling the hollow body section with fluid, sealingly closing the second open end by movably inserting a second element in the second open end, supportably encompassing the first and second ends of the hollow body section and applying a required test pressure within the hollow body section by dynamically moving the first and second elements toward each other through the first and second open ends such that a sudden pressure build-up occurs. For applying the required test pressure, a weight is accelerated toward the second element such that it impacts the second element at an impact velocity, thereby dynamically moving the first and second pistons toward each other with the features in the main claim. Advantageous further developments as well as a testing arrangement for implementing the process are the subject of subclaims.

The advantage of the process according to the invention is that cost-intensive test body preparations, such as, welding closed the open ends of the hollow body section, are not required and even serial tests can be performed simply. It is also advantageous that, compared with known conventional testing, the process according to the invention supplies more realistic results in simulating dynamic internal pressure loading.

As a rule, a virtually incompressible liquid, such, for example, as, oil or alcohol, is used as the fluid. However, in keeping with safety regulations, a gas, such as, air, can instead be used. A vertical arrangement of the test setup, wherein gravity is used for the falling weight, has proved advantageous. However, it is equally conceivable to arrange the test setup horizontally and to use a movable weight instead of a falling weight. The weight could be suitably accelerated, via, for example, a stressed spring. The arrangement of a piston movable toward an abutment has practical advantages. In principle, both pistons could be used, by the striking from above of two separate weights.

DETAILED DESCRIPTION OF THE PREFERRED EMBODIMENTS

Figure 1:
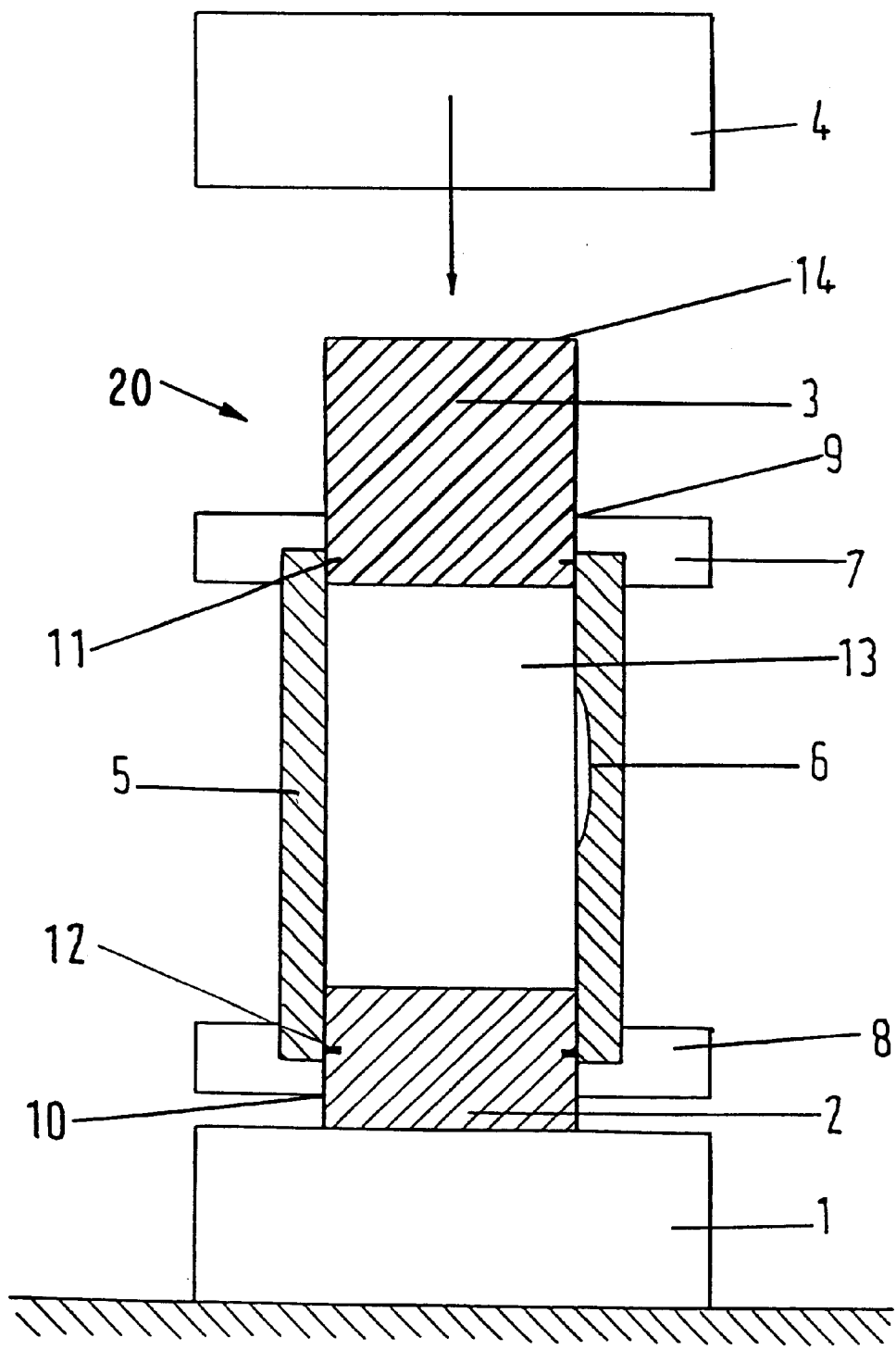
FIG. 1 shows a test setup according to an embodiment of the present invention.

The drawing shows, schematically and in longitudinal section, the essential elements of the test setup 20 according to the invention. This test setup 20 includes an abutment 1 and a piston, which stands on the abutment 1 and is movable in a hollow body section 5 to be checked. Located at in opposite side of the hollow body section 5 to and at a distance from this piston 2 is another movable piston 3, which is pressurized in this example by a falling weight 4. The details of the suspension and guidance of the falling weight 4 are omitted here, because they are not essential to the invention. The hollow body section 5 to be checked can have a target fracture point, such as, for example, as in the form of a nick 6 created before testing. Each end of the hollow body section 5 is supported by an encompassing support ring 7, 8. The two support rings 7, 8 are intended to prevent the premature expansion of the hollow body section 5 at its ends and the pressure drop that would be associated with this. The two pistons 2, 3 extend through openings 9, 10 in the respective support rings 7, 8 and are sealed in the hollow body section 5 by seals 11, 12. The interior of the hollow body section 5 is filled with a fluid 13. An incompressible fluid such as oil is preferably used as fluid 13. However, a gas such as air may also be used instead.

The testing procedure is described in what follows. The hollow body 5 to be tested is plane-parallel at its two end faces, so that the support rings 7, 8 come to rest at each end. In addition, depending on requirements, a target fracture point, such as a nick 6, may optionally be located on the interior wall of the hollow body section 5.

First, the lower piston 2 with the sealing ring 12 is placed into the hollow body section 5, and the lower support ring 8 is slipped on. The interior of the hollow body section 5 is then filled with the fluid 13, for pressure transmission. After this, the upper piston 3 with the sealing ring 11 is introduced into the hollow body section 5, and the upper support ring 7 is slipped on. The test body 5 prepared in this manner is positioned on the abutment 1. After release of a lock (not shown), the falling weight 4, which is guided in an arrangement not described here in greater detail, falls onto the upper end face 14 of the upper piston 3. The impact energy input by the falling weight 4 is so designed such that, the sudden internal pressure increase in the hollow body section 5 either bursts, the hollow body section 5 or achieves a preestablished load.

After disassembly of the test setup 20 including the removal of the pistons 2, 3 with the seals 11, 12, the support rings 7, 8 and the fluid 13 that remains in the hollow support body 5, it is possible, if a burst has occured, to determine the maximum circumferential strain in the failure region and to evaluate the appearance of the fracture area.

What is claimed is:

1. A process for pressure checking a hollow body section having a first open end and a second open end, comprising the steps of:
   closing the first open end of the hollow body section by sealingly movably inserting a first element in the first open end;
   filling the hollow body section with a fluid;
   closing the second open end of the hollow body section by sealingly movably inserting a second element in the second open end;
   supporting the first and second open ends of the hollow body section; and
   applying a required test pressure within the hollow body section by dynamically moving the first and second elements toward each other through the first and second open ends such that a sudden pressure build-up occurs.

2. The process of claim 1, wherein said step of applying a required test pressure comprises applying a required bursting pressure.

3. The process of claim 1, further comprising the step of providing the hollow body section with a target fracture point before said step of applying a required test pressure.

4. The process of claim 1, wherein said step of applying a required test pressure comprises the step of accelerating a weight toward the second element such that the weight impacts the second element at an impact velocity thereby dynamically moving the first and second elements toward each other.

5. A test setup for pressure checking a hollow body section having a first open end and a second open end, comprising:
   a stationary abutment;
   a first piston resting on said stationary abutment and sealingly movably insertable in the first open end of the hollow body section;
   a second piston sealingly movably insertable in the second end of the hollow body section;
   a fluid insertable in said hollow body section between said first piston and said second piston;
   first and second support rings supportably engagable on the first and second open ends of the hollow body section for encompassing said first and second open ends; and
   a movable object movably acceleratable toward said second piston under one of a gravitational or resilient urgency for imparting a dynamic internal pressure loading to the hollow body section upon impact of said movable object with said second piston.

6. The test setup of claim 4, wherein said movable object comprises a falling weight.

7. The test setup of claim 4, wherein said movable object comprises a horizontally movable weight.

* * * * *